US009072456B2

(12) United States Patent
Boe (10) Patent No.: US 9,072,456 B2
(45) Date of Patent: *Jul. 7, 2015

(54) MODULAR HEADREST AND MULTI-LIGHT APPARATUS

(71) Applicant: Irwin N. Boe, Shawnee, KS (US)

(72) Inventor: Irwin N. Boe, Shawnee, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/694,282

(22) Filed: Nov. 15, 2012

(65) Prior Publication Data

US 2013/0150683 A1      Jun. 13, 2013

Related U.S. Application Data

(63) Continuation of application No. 12/802,217, filed on Jun. 2, 2010.

(51) Int. Cl.
| | | |
|---|---|---|
| *A61B 1/07* | (2006.01) | |
| *A61B 5/00* | (2006.01) | |
| *A61B 1/24* | (2006.01) | |
| *F21V 8/00* | (2006.01) | |
| *A61B 1/06* | (2006.01) | |
| *A61B 1/00* | (2006.01) | |
| *A61G 15/12* | (2006.01) | |
| *A61B 1/12* | (2006.01) | |

(52) U.S. Cl.
CPC ................. *A61B 1/07* (2013.01); *A61B 5/0077* (2013.01); *A61B 1/24* (2013.01); *A61G 15/125* (2013.01); *G02B 6/0008* (2013.01); *A61B 5/6891* (2013.01); *A61B 5/0088* (2013.01); *A61B 1/0669* (2013.01); *A61B 1/0684* (2013.01); *A61B 1/128* (2013.01); *A61B 1/00147* (2013.01)

(58) Field of Classification Search
CPC ............. A61B 1/00147; A61B 1/0669; A61B 1/0684; A61B 1/07; A61B 1/128; A61B 1/24; A61B 5/0077; A61B 5/0088; A61B 5/6891; A61G 15/125; G02B 6/0008
USPC .......... 250/504 H, 504 R; 362/131, 430, 431, 362/572–574; 385/115
See application file for complete search history.

(56) References Cited

U.S. PATENT DOCUMENTS

| | | | |
|---|---|---|---|
| 3,726,012 A | | 4/1973 | Grayson et al. |
| 4,149,086 A | | 4/1979 | Nath |
| 4,233,649 A | * | 11/1980 | Scheer et al. ................. 362/131 |
| 5,281,134 A | | 1/1994 | Schultz |
| 6,089,740 A | | 7/2000 | Forehand et al. |
| 6,290,713 B1 | | 9/2001 | Russell |
| 6,413,268 B1 | | 7/2002 | Hartman |
| 6,719,447 B1 | | 4/2004 | Woodward et al. |
| 7,884,341 B2 | * | 2/2011 | Boe .............................. 362/573 |
| 2004/0061038 A1 | | 4/2004 | Solich |
| 2005/0286845 A1 | | 12/2005 | Plocharczyk |
| 2006/0285316 A1 | | 12/2006 | Tufenkjian et al. |

* cited by examiner

*Primary Examiner* — Stephen F Husar
(74) *Attorney, Agent, or Firm* — Aaron S. Reed; Erickson Kernell Derusseau & Kleypas, LLC (57) ABSTRACT

A multi-light apparatus (10) for primary use in dental or medicinal operatory workspaces and for interconnection with a modular operating chair (12), so as to form the headrest thereof, preferably includes first and second radiation sources (36,72) and a selection mechanism (70) for selecting a desired radiation source, a rigidly flexible light pipe (16) that may be alternatively coupled to each light source (36,72) and is configured to transmit selected radiation to a patient (14), a reflective surface (78) configured to direct the selected radiation to the pipe (16), a power supply (50), a cooling fan (56), and at least one potentiometer (66,68) for varying the voltage delivered to the sources (36,72) and fan (56).

18 Claims, 8 Drawing Sheets

FIG. 14

MODULAR HEADREST AND MULTI-LIGHT APPARATUS

RELATED APPLICATIONS

The present U.S. non-provisional patent application claims priority of an earlier-filed application of the same title, Ser. No. 12/802,217, filed Jun. 2, 2010, which was a continuation-in-part application of an even earlier-filed application which issued into a patent of the same title, U.S. Pat. No. 7,884,341, filed Apr. 28, 2007. The contents of the identified earlier-filed application and patent are hereby incorporated by reference into the present application. To the greatest extent possible, the applicant hereby rescinds and disclaims any arguments or admissions or other statements or actions, whether implied or expressed, that may have given rise to prosecution history estoppel in the identified earlier-filed application or any other related applications.

BACKGROUND OF THE INVENTION

1. Technical Field

The present invention relates to apparatuses, systems, and methods of illuminating and/or providing alternative radiation to a dental or medicinal patient. More particularly, the present invention relates to a multi-light apparatus adapted for use and interconnection with a modular dental or, medical chair, and comprising at least one light source, a housing cooperatively configured with the chair to present the headrest thereof, and a rigidly flexible light pipe coupled to the source and presenting an adjustably repositionable outlet.

2. Background Art

Peripheral lighting apparatuses and instruments have long been developed to serve the critical task of illuminating dental and medicinal operatory areas. More recently, specialty lighting techniques have also been developed that aid in curing photo-initiated compounds, treating various surficial ailments, and enabling other radiation based functions such as transillumination in dentistry. Examples of conventional overhead apparatuses and systems can be seen in FIG. 27 of U.S. Pat. No. 7,139,068, and commercially include Lucent and Advanced Operatory Lights sold by Thompson Dental Equipment of Gavilan Hills, Calif. While enabling visibility, the addition of these often bulky lighting apparatuses in the workspace and usually in close proximity to the patient has resulted in various practical concerns.

For example, increased crowding in the workspace often causes inconvenience to an operator, such as the treating dentist, doctor, nurse, or technician. Where the instrument affects performance or hinders access to the patient, it may further present a danger. In some instances, inconvenience to operators may be also caused by asymmetric configurations, and more particularly, by non-interchangeable left- and right-handed configurations. Of further concern, overhead apparatus often present only incremental adjustment capabilities, especially where limited by tracks and/or guides. Thus, it is appreciated by those of ordinary skill in the art that these concerns combine to reduce the efficiency of operation.

Portable lighting apparatuses have been developed, such as are commercially available from DNTLworks Equipment Corporation of Centennial, Colo., under the Fiber Optic Operatory Light product line, which reduce workspace obstruction. However, these portable devices also include a wheeled floor stand, tripod, or other structure for support. As such, additional appurtenances are still necessary within the workspace, and the same concerns are present albeit to a lesser extent.

A few hand-held lighting devices have, likewise, been introduced to further reduce obstruction and increase freedom of movement. These devices, such as the instruments presented in U.S. Pat. Nos. 6,918,762 and 6,419,483, typically include a light source within a hand-held casing, collimating, reflecting, and/or filtering means to organize the light generated by the source, and an outlet for directing the light toward the patient. However, these devices also result in inconvenience to the operator primarily in that one hand must be occupied to hold the light. Where an additional staff member is utilized to hold the device laborious costs are incurred. Finally, it is appreciated that these devices are typically relegated to curing light and other low power output applications, as significant measures would have to be taken to protect the operator from the large quantities of heat energy generated during incandescence light production.

SUMMARY OF THE INVENTION

Responsive to these and other concerns, the present invention provides a novel headrest and multiple light apparatus. The invention is useful among other things for reducing workspace obstruction by replacing a conventional headrest with the inventive apparatus. As a result virtually no additional support structure is introduced within the operatory workspace. The apparatus is further useful for providing increased adjustability and maneuverability pertaining to the point of light emission. Finally, the apparatus is further useful for providing multiple light sources for performing a variety of functions, including illumination, curing, and bleaching.

A first aspect of the invention concerns an operational light apparatus adapted for use and interconnection with a modular operating chair, and for illuminating a patient positioned within the chair. The apparatus includes a light source configured to produce a quantity of light having a minimum luminosity value when energized. Also included is a light pipe defining an inlet communicatively coupled to the light source, a longitudinal pipe length, and an outlet positioned at a first location and configured to transmit the light towards the patient. A housing configured to retain the light source, connected to the pipe at or near the inlet, and presenting a soft exterior surface is also included. Finally, a power supply communicatively coupled to and operable to energize the light source is provided. The housing and chair are cooperatively configured such that the housing presents the headrest of the chair when interconnected, and the soft exterior surface engages the head of the patient when the patient is positioned within the chair.

A second aspect of the invention further concerns a multi-light apparatus adapted for use and interconnection with a modular operating chair, and for selectively producing and engaging the patient with multiple types of radiation. In this configuration, the apparatus includes at least one light source configured to produce a plurality of differing types of radiation when energized, and a selection mechanism is configured to cause the light source to produce a selected radiation type. A light pipe defining an inlet able to be communicatively coupled to each of said at least one light source is further provided. A housing is configured to retain said at least one light source, and is connected to the pipe at or near the inlet.

Further disclosure is made as to preferred and exemplary embodiments of the invention including the provision of a cooling mechanism such as a fan retained within the housing, an ultra-violet light source, and a selection mechanism including a dial for choosing between and energizing the light sources. These and other features of the present invention are discussed in greater detail in the section below entitled DESCRIPTION OF THE PREFERRED EMBODIMENT(S).

BRIEF DESCRIPTION OF THE DRAWINGS

Preferred embodiments of the invention are described in detail below with reference to the attached drawing figures, wherein.

DETAILED DESCRIPTION OF THE PREFERRED EMBODIMENT(S)

Figure 1:
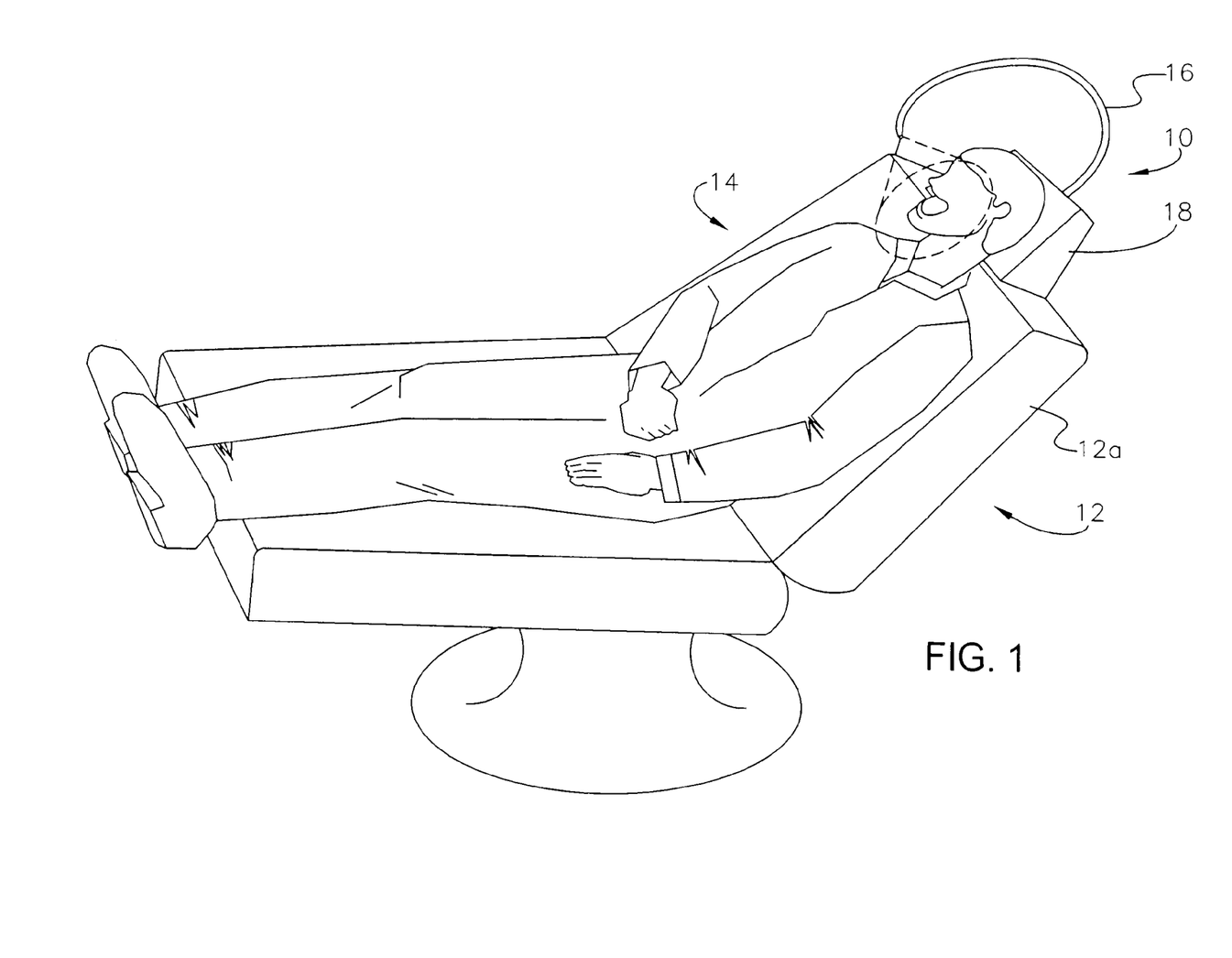
FIG. 1 is a perspective view of a modular headrest and operational light apparatus in accordance with a preferred embodiment of the invention, particularly illustrating the engagement of the apparatus with an operational chair and patient.

As illustrated and described herein, the present invention relates to a headrest and light apparatus 10 adapted for use and interconnection with a modular operating chair 12. The apparatus 10, as shown in FIG. 1, is configured to illuminate a patient 14 within a desired operatory area. It is the primary intent of the invention for the apparatus 10 to be utilized in the dental and medical professions; however, it is within the ambit of the invention for the apparatus 10 to also be used in other modular-chair based environments where minimal workspace obstruction and a highly adjustable light source is desired. Where not further described herein materials and/or methods of manufacture or construction shall be deemed to involve conventional and future equivalent means.

1. Modular Headrest and Operational Light Apparatus

Figure 2:
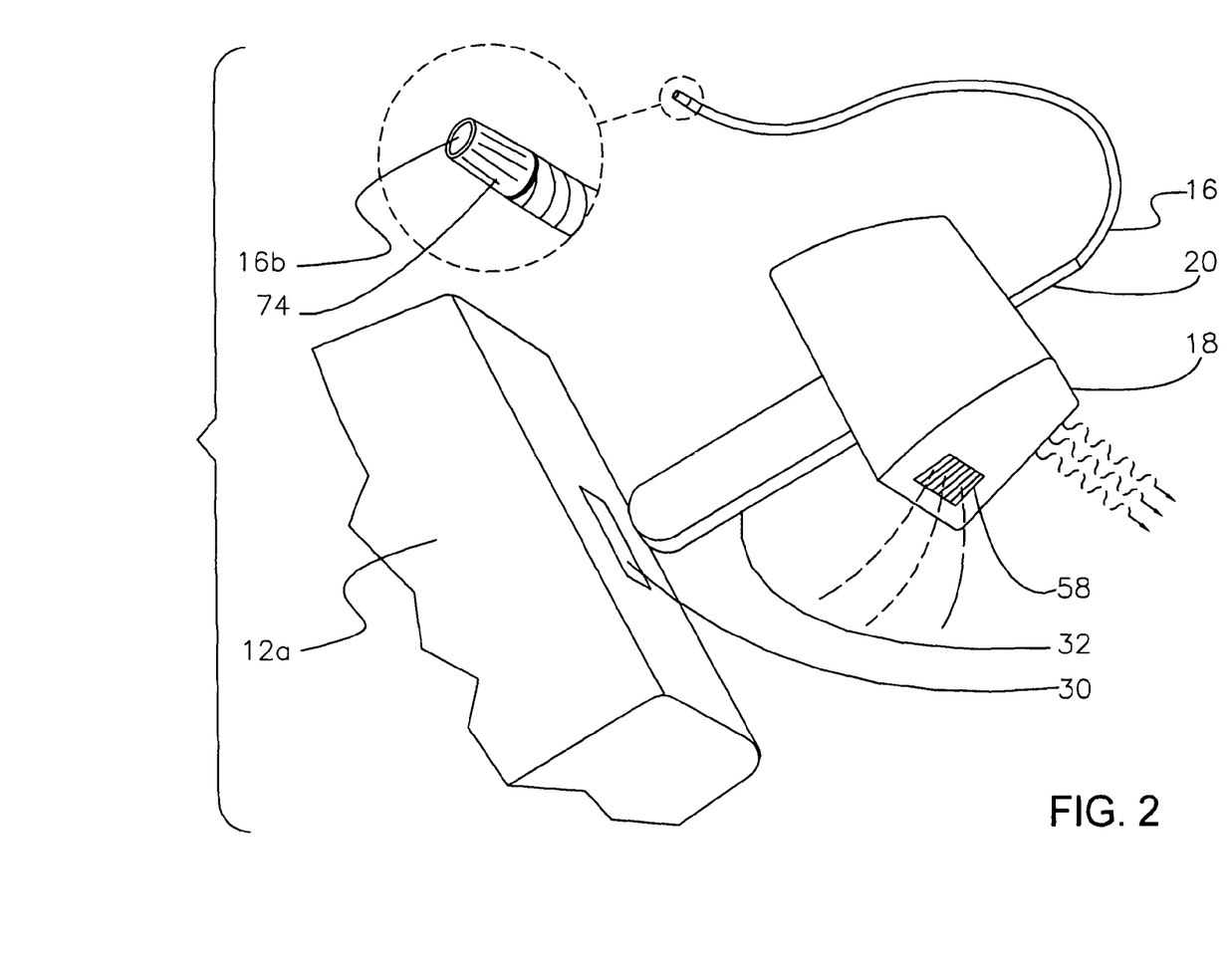
FIG. 2 is an enlarged perspective view of the apparatus shown in FIG. 1, particularly illustrating the headrest disconnected from the backrest of the chair, an adjustable pipe tip, and cooling airflow patterns.
Figures 3, 4, 4A:
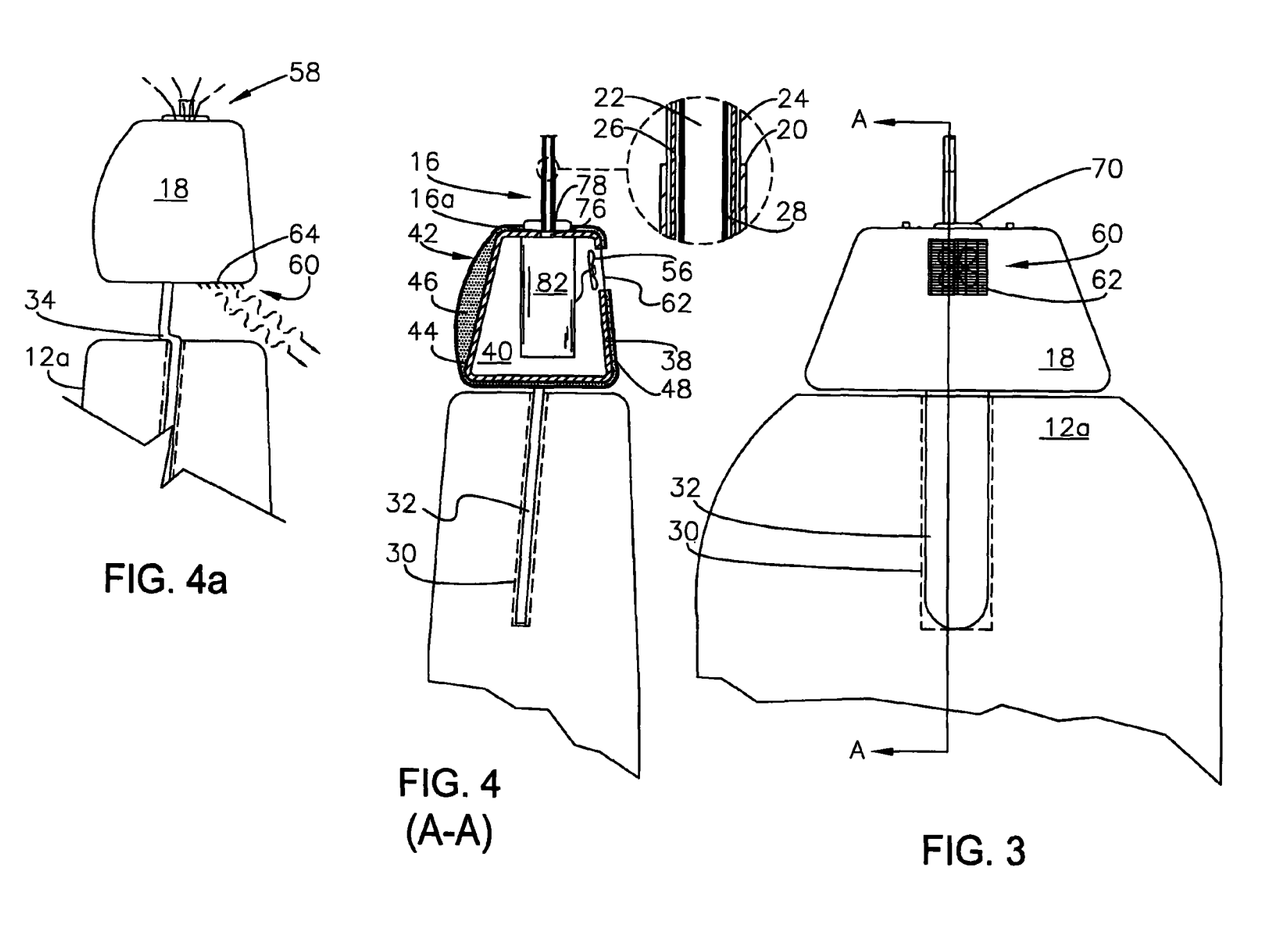
FIG. 3 is a rear elevation of the apparatus shown in FIG. 1, particularly illustrating a cooling fan, airflow outlet, and male connection prong.
FIG. 4 is a cross-section of the apparatus as delineated by section A-A in FIG. 3, further illustrating a housing, an interior protective sleeve, the fan, outlet and prong.
FIG. 4a is a fragmentary side elevation of the apparatus and chair in accordance with a preferred embodiment of the invention, particularly illustrating the illuminator/headrest being spaced from the back rest by a bent male connecting prong, and alternative cooling air-flow patterns facilitated thereby.

As best shown in FIGS. 1, 2, and 4, the apparatus 10 generally includes a light pipe 16 presenting a light receiving inlet 16a, light emitting outlet 16b at a first location, and an illuminator/headrest 18 connected to the light pipe 16 and interconnectable with the operatory chair 12. The pipe 16 preferably presents a rigidly flexible structure; whereas the phrase "rigidly flexible," as used herein, shall mean able to be manually, repeatedly, and inelastically bent into one of a plurality of functional conditions wherein the outlet is securely repositioned.

The preferred pipe 16 further presents a longitudinal pipe length sufficient to effect the intended purpose. For example, as illustrated in FIG. 1, where utilized to illuminate the oral cavity of a patient, the pipe length is preferably within the range of 60 to 120 cm (i.e., approximately 2 to 4 ft), so as to be manipulable around the head of the patient 14. To further avoid contact with the patient's head, the pipe 16 preferably presents a non-flexible section (i.e., "extender") 20 adjacent the illuminator 18 (FIG. 2). The non-flexible pipe section 20 may be formed of a rigid material, such as metal, aluminum or a hard plastic, or may present an exterior sleeve that is fixedly attached to the illuminator 18 and extends along the pipe 16 for a predetermined length. More preferably, the non-flexible section 20 presents a length within the range of 10 to 20 cm.

As shown in FIG. 4, the preferred pipe 16 may include a fiber optic core 22 and an exterior sheath 24 configured to form superjacent layers with at least a portion of the core 22. The sheath 24 is inelastically bendable and self-supporting, i.e. able to hold its shape. In a preferred embodiment, the sheath 24 includes at least one, and more preferably, a plurality of symmetrically spaced bendable wires 26 having a longitudinal axis parallel with the central axis of the pipe 16. The preferred pipe 16 further includes a flexible opaque layer 28 preferably intermediate the core 22 and sheath 24. The layer 28 preferably presents a light-reflective surface adjacent the core 22 so that no light is absorbed thereby. In a preferred embodiment, where the layer 28 is included, the sheath 24 extends only along a portion of the core 22 adjacent the inlet 16a, so that a more flexible and easily manipulated portion of the pipe 16 is presented adjacent the outlet 16b.

As shown in FIGS. 1 through 4, the preferred illuminator 18 is configured to be interconnected with the backrest 12a of the operatory chair 12 in lieu of a conventional headrest. The illuminator/headrest 18 is preferably removably interconnected to the backrest 12a; wherein the term "removably interconnected" shall mean able to be manually dismantled by a human user without the aid of a tool. As it is appreciated by those in the relevant arts that conventional operatory chairs generally present universal interconnection mechanisms and dimensions, it is more preferable and an intended benefit of the invention for the illuminator 18 to be configured so as to be interconnectable with conventional chairs 12 and thereby more easily implemented in existing operatory settings.

As shown in FIG. 2, for example, where the conventional chair 12 presents a universal female receptacle 30, the apparatus 10 preferably includes a male prong 32 configured to be tightly received by the receptacle 30. For example, where the receptacle 30 presents a planar rectangular cross-section that extends within the backrest 12a a depth not less than one-third the longitudinal length of the backrest 12a (FIGS. 3 and 4), the prong 32 preferably presents a similar rectangular cross-section having dimensions slightly less than (e.g., 95 percent of) the cross-sectional dimensions of the receptacle 30. The prong 32 is formed of a durable rigid material such as steel, aluminum, or a hard plastic (e.g., polyvinyl chloride).

In an alternative embodiment, the prong 32 presents a longitudinal bend 34 that forms a seat with the backrest 12a when fully inserted, as shown in FIG. 4a. This configuration results in a gap sufficient for improving airflow to and from the illuminator 18. More preferably, the bend 34 is located, so as to result in a 5 to 15 cm spacing between the illuminator 18 and the backrest 12a.

The illuminator 18 functions to provide a soft comfortable interface for engaging the head of the patient 14, and to generate a desired type and quantum of radiation. In a preferred embodiment; the illuminator 18 is configured to generate visible light (i.e., radiation having wavelengths within the range 400 to 700 nm) at a sufficient intensity to illuminate a desired portion of the patient. For example, in a dentistry application, it may be desired to illuminate the oral cavity and immediately surrounding areas of the patient. As such, the illuminator 18 includes a light source 36 (FIGS. 5 through 6a) that is communicatively coupled to the inlet 16a of the pipe and configured to produce light having a minimum luminosity value, and more preferably a lumens output not less than 100 and most preferably not less than 500, as measured at the outlet 16b of the pipe when energized. In this configuration, the preferred light source 36 may present a 50-watt dual pin halogen lamp light bulb or a high intensity LED lamp powered by a 12V power supply.

Returning to FIG. 4, the illuminator 18 includes a housing 38 that provides the structural capacity thereof, and defines an interior space 40 wherein the functional components, including the light source 36, are retained. The preferred housing 38 presents a polygonal configuration and is securely connected to the light pipe 16 and male prong 32 preferably along opposite planar surfaces. In a preferred embodiment, both the prong 32 and pipe 16 are not integrally attached to the housing 38, so as to be removable and thereby easily replaceable; for example, where a male prong having differing dimensions is needed to connect to a second chair. However, it is appreciated that the male prong 32 may be integrally formed (e.g., cast molded) with at least a portion of the housing 38 where desired. The housing 38 is preferably rotatably connected to the pipe 16 at or near the inlet 16a. The inlet 16a is preferably adjacent or slightly disposed within the space 40 directly above the light source 36.

As previously mentioned, the illuminator 18 presents a soft exterior surface for engaging the head of the patient 14. In a preferred embodiment, a multi-layer exterior cover 42 forms superjacent layers with at least the exterior surface of the housing that engages the patient's head. More preferably, the cover 42 overlays the entire exterior surface of the housing, except for the provisions further described herein, such as, for example, a top orifice for receiving the inlet 16a of the pipe. As shown in FIG. 4, the preferred cover 42 consists essentially of a thermo-insulating interior layer 44, a soft intermediate cushion layer 46, and a flexible yet durable exterior layer 48 (e.g., leather) that is non-reactive to human skin and the substances anticipated to be encountered in a given operatory settings, such as water, saline-solution, blood, etc. It is appreciated that two or more of the layers 44-48 may be combined; for example, wool felt or an equivalent soft synthetic material that is both soft and thermally insulating may supplant the inner layers 44,46.

Figure 5:
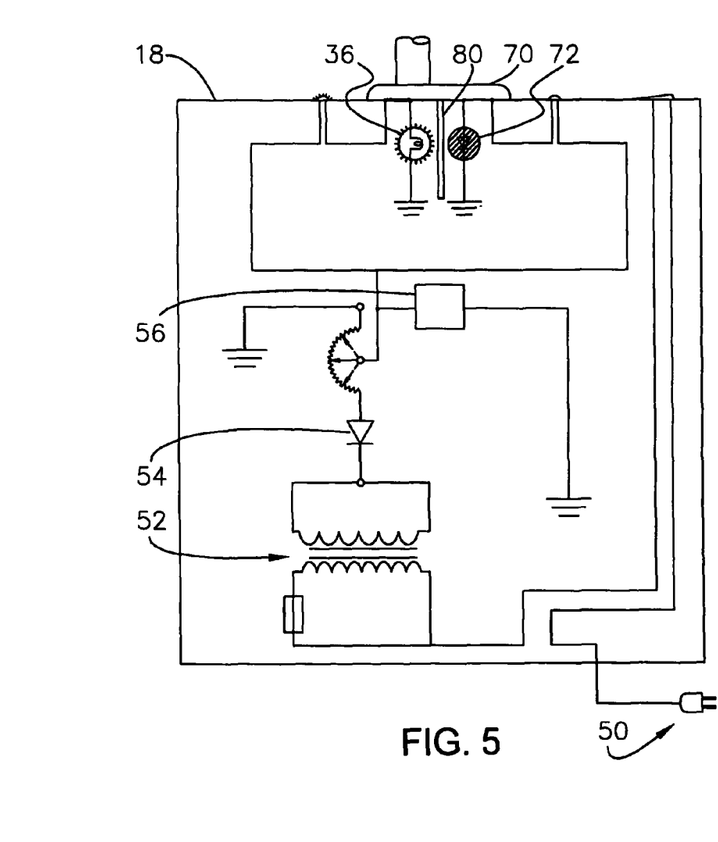
FIG. 5 is an electrical schematic and diagrammatic elevation of the innerworkings of the illuminator in accordance with a preferred embodiment of the invention, particularly illustrating first and second light sources, a transformer, a potentiometer, and an alternating current adaptor.
Figure 6:
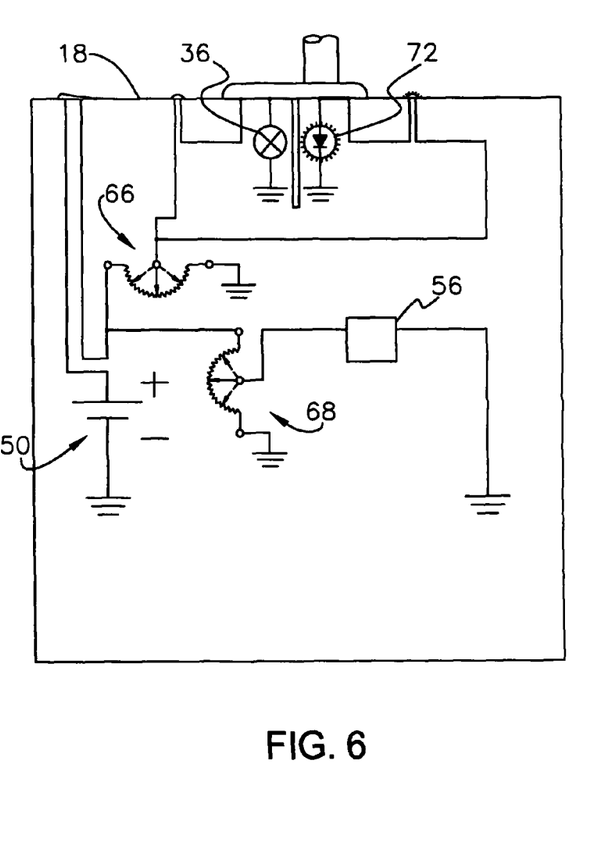
FIG. 6 is an electrical schematic and diagrammatic elevation of the innerworkings of the illuminator in accordance with a preferred embodiment of the invention, particularly illustrating dual potentiometers, and a battery power supply.

The illuminator 18 includes a power supply 50 at least partially retained within the housing 38 and communicatively coupled to and operable to energize the light source 36 (FIGS. 5 and 6). For example, the power supply 50 may present a 12V battery (FIG. 6). In addition to or in lieu of batter power, the power supply 50 may be configured to connect to a standard wall 120V alternating current source; and as such, may include an adaptor chord and plug (FIG. 5), a transformer 52 for stepping down the charge, and a rectifier 54 for converting to direct current. More preferably, a dual power supply 50 is redundantly provided having both a battery and AC adapting elements. In this configuration, the battery is preferably coupled to and rechargeable by the AC adapting elements.

Especially where incandescent light production is provided, the preferred illuminator 18 is further configured to dissipate and direct heat associated with the generation of the desired radiation away from the patient 14, and as such includes a cooling mechanism 56. In the illustrated embodiment, a miniature fan retained within the housing 38, and coupled to the power supply 50 presents the cooling mechanism 56 (FIGS. 5 and 6). In this configuration, the housing 38 defines at least one intake opening 58 spaced from and at least one outlet opening 60 adjacent the fan 56 (FIGS. 2 through 4a). The fan 56 and said at least one inlet and outlet openings 58,60 are cooperatively configured to draw ambient air into the housing 38 and expel heated air out of the housing 38 at a minimum rate, and more preferably at a rate not less than 10 cfm. The fan is preferably quiet during operation.

As shown in FIG. 2, the intake 58 may be presented by a plurality of vertical slat openings or louvers defined by the lowermost third of the sides of the housing 38. The outlet 60 may be presented by a window defined by the uppermost third of the rear panel of the housing 38 (FIG. 3). It is appreciated in this configuration that ambient air would be drawn in from the front of the illuminator 18 and to the left and right of the patient 14, which further provides the benefit of creating a gentle breeze that comforts the patient 14. The air then flows through the space 40 moving upward and towards the top of the rear panel, where it is expelled by the fan 56 through the outlet 60 in an opposite direction from the patient 14. Finally, screens 62 configured to allow the passage of air but not large air-borne particles or other foreign objects preferably protect both the intake and outlet openings 58,60.

Figures 6A, 7, 7A:
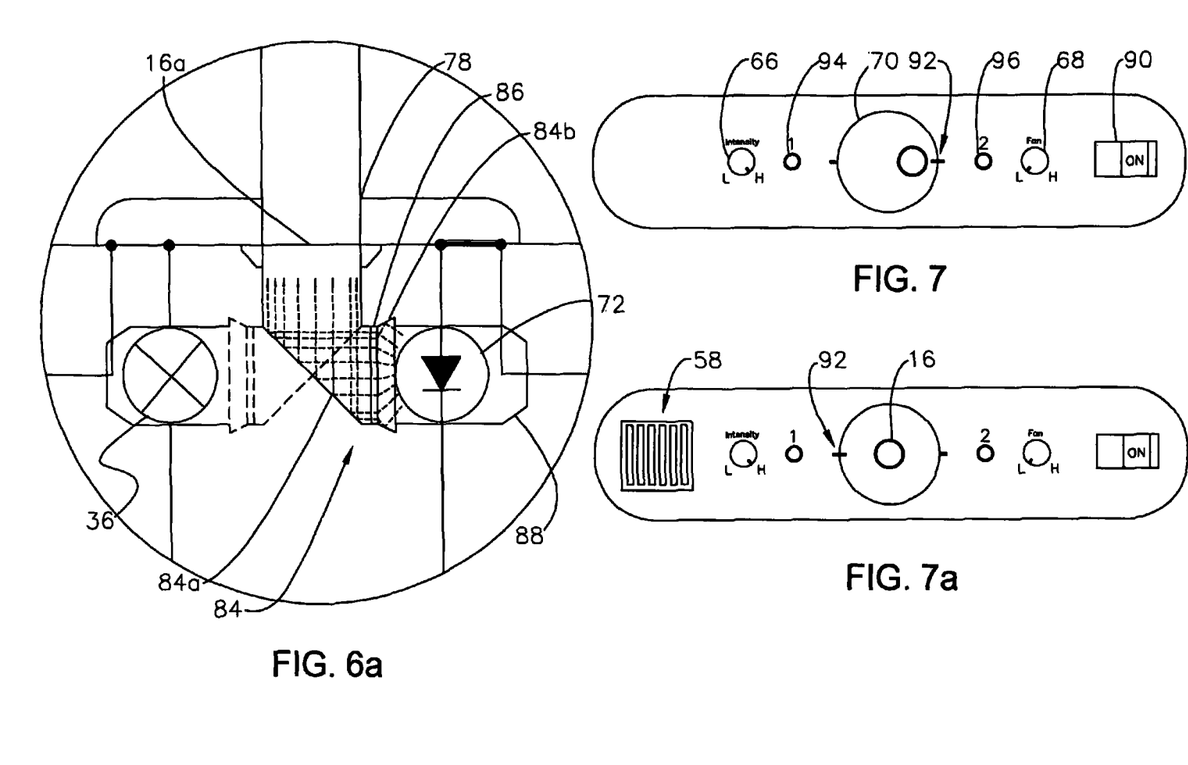
FIG. 6a is a partial diagrammatic elevation of the innerworkings of the illuminator in accordance with a preferred embodiment of the invention, wherein a rotatable tubular member having a reflective surface is presented intermediate and configured to engage the selected first or second light source.
FIG. 7 is a planar view of the top surface of the apparatus in accordance with a preferred embodiment of the invention, particularly illustrating a main on/off switch, first and second light source indicators, light source and fan potentiometers, and a light actuating and pipe orienting dial.
FIG. 7a is a planar view of the top surface of the apparatus in accordance with a preferred embodiment of the invention, particularly illustrating an air inlet, a main on/off switch, first and second light source indicators, light source and fan potentiometers, and a light actuating and mirror positioning dial.

As alternatively shown in FIGS. 4a and 7a, the intake 58 may present a plurality of slats or louvers defined by the uppermost panel of the housing 38 (FIG. 7a), while the outlet 60 is defined by the lowermost panel of the housing 38. As such, in this configuration, the fan 56 is positioned adjacent the lowermost panel and aligned with the outlet 60, so that air flows from the top of the housing 38 into the space 40 and out the bottom panel. It is appreciated that the gap between the headrest 18 and backrest 12a provided by the bent prong 34 facilitates airflow in this configuration. In this configuration, the preferred outlet 60 further present a series of diagonally distending guides 64 for throwing the heated air away from the patient 14.

As shown in FIG. 6, the preferred illuminator 18 also includes a potentiometer or a digitally controlled potentiometer (DCP) 66 intermediately coupled to the power supply 50 and light source 36, and a second potentiometer 68 between the power supply 50 and fan 56. As is known in the art, the potentiometers 66,68 function to adjust the voltage delivered to the light source 36 and fan 56 by changing the resistance within the circuit, so as to vary their intensity and rpm, respectively. Rotary potentiometers are shown in FIGS. 7 and 7a; however, it is appreciated that other configurations such as faders may be utilized instead. Alternatively, and as shown in FIG. 5, since the amount of light is directly proportional to the amount of heat generated and therefore the need for cooling airflow, a single potentiometer may be connected in series between the power supply 50 and both the light source 36 and fan 56.

2. Modular Headrest and Multi-Light Source Apparatus

More preferably, the illuminator 18 is further configured to be capable of providing at least one other type of radiation (excluding heat energy) when desired, and as such presents a "multi-light" apparatus. In this regard, at least one light source is configured to produce a plurality of differing types of radiation when energized. A single light source may be individually combined with a plurality of optical filtering, reflecting and/or modifying sets (not shown) as selected, such as is disclosed by U.S. Pat. No. 4,608,622 (incorporated by reference herein), to cooperatively produce a plurality of differing radiation products. A selection mechanism 70 is coupled to said at least one light source and configured to cause the light source to produce a selected radiation type (FIG. 5). In the '622 patent, for example, such a mechanism is presented by a turntable connected to the sets. Thus, the need to have a separate light apparatus, such as a dental curing light, in the operatory workspace is eliminated.

More preferably, a plurality of light (i.e., radiation) sources is utilized to reduce complexity. In the illustrated embodiment, a second light source 72 is further included (FIGS. 5 through 6a), with the understanding that yet additional light sources could be similarly provided and configured. The preferred second source 72 is configured to produce a second type of radiation selected from the group consisting of blue light, near, far and extreme ultra-violet radiation, and x-ray radiation. For example, for dental applications, the second light source 72 is preferably configured to produce ultra-violet and to a lesser extent blue radiation having wavelengths within the range 250 to 500 nm for use in photo-polymerization. It is appreciated by those of ordinary skill in the art that at these wavelengths common curing initiators, such as Camphorquinone (CQ) and Phenyl propanedione (PPD) are activated.

The second source 72 may therefore utilize technology selected from the group consisting of quartz-tungsten-halogen, argon laser, plasma-arc (PAC), light-emitting diode, multi-spectrum LEDS, and similar variants or combinations thereof, with the understanding that different technologies will present different characteristics and concerns relating to the range of output wavelengths, amount of heat and infrared by-product, operational and replacement costs, irradiance (mW/cm2), and useful life, etc. It is also appreciated that filters such as dichroic reflectors (not shown) may be utilized to form a band-pass that eliminates unwanted wavelengths of radiation produced by a particular technology.

As shown in FIGS. 5 and 6, the light pipe 16 is interchangeably used for both visible light and alternative radiation source applications. As such, the pipe length is of sufficient value not only to illuminate, but to also enable the outlet 16b to enter and be manipulated within the oral cavity as is necessary to effectively deliver the alternate radiation. It is yet further appreciated that the outlet size is indirectly proportional to the irradiance provided by the second source 72. As such, the outlet 16b is not only sized to provide sufficient illumination in the visible light mode, but to also result in sufficient irradiance and collimation when applying the alternative radiation source 72. In a preferred embodiment, the outlet 16b presents a cross-sectional area not less than 1.5 cm2. The preferred outlet 16b is adjustable between one of a plurality of configurations either by interchangeably replacing a distal portion of the pipe 16 or by rotating a dual mode tip 74 (FIG. 2). For example, the tip 74 may present in a first position collimating or reflective characteristics that increase collimation for curing, and maximally reduce this effect in a 90 degree offset position so as to spray visible light.

The light sources 36,72 are positioned and oriented so as to each be communicatively coupled to the inlet 16a of the light pipe, individually. As shown in FIGS. 5 through 6a, the light sources 36,72 may be positioned at or near the top and about the vertical central axis of the housing 38. In a preferred embodiment, the selection mechanism 70 presents a dial rotatably connected to the top surface of the housing 38. The dial 70 is co-axially aligned with the vertical central axis, and is diametrically configured relative to the spacing of the sources 36,72, so as to overlay both. Dual orifices 76 are defined by the housing 38 adjacent each of the sources 36,72, and an orifice 78 through which the pipe inlet 16a is eccentrically connected is defined by the dial 70 as shown in FIG. 4, so that the inlet 16a may be alternatively coupled to each of the sources 36,72.

In the illustrated embodiment, the preferred dial 70 is further configured to activate and cause to be energized the selected light source 36 or 72 (FIGS. 5 and 6). More particularly, wire leads feeding each of the sources 36,72 are interrupted adjacent the dial 70. The dial 70 includes at least one conductive branch positioned and oriented to contact the leads and complete the respective circuit only when the dial orifice and inlet 16a are properly aligned with the source orifice, so that the dial 70 presents a rotary switch.

A heat shield 80 preferably distends from the top of the housing 38 and between the sources 36,72, so that damage caused by heat generated during the operation of the other is reduced. Similarly, as shown in FIG. 4, a protective sleeve 82 is also preferably included within the space 40, and configured to form a barrier between the outlet and inlet 58,60 and the radiation sources 36,72, so that the radiation is contained within the housing 38.

In an alternative embodiment, the dial 70 may be fixedly connected to at least one reflective surface distending within the housing 38. The reflective surface is configured to reflect at least a portion of the selected radiation product towards the inlet 16a (FIG. 6a). In this configuration, the pipe 16 is preferably co-axially aligned with the dial 70 and vertical central axis (FIGS. 6a and 7a). More preferably, the reflective surface is presented by the interior surface of an L-shaped tubular member 84 that distends from the dial 70 (FIG. 6a) in lieu of the heat shield 80. A chamfered bend 84a is provided at the elbow of the member 84. The bend 84a presents an interior reflective surface having a forty-five degree slope, so that horizontally projected radiation is redirected ninety-degrees upwards towards the inlet 16a directly above. It is appreciated that the slope angle changes for non-horizontal angles of incident. To facilitate this function, the preferred member 84 further includes a flared end section 84b for funneling light interiorly and a collimating element (e.g., lens) 86 adjacent the end section 84b for collimating the rays of light prior to reaching the bend 84a. Opposite the member 84 each of the sources 36,72 may be further paired with a rear reflective closed tubular section 88 for further directing radiation towards the inlet 16a.

In operation, once the patient 14 is properly positioned within the chair 12, the power supply 50 of the illuminator 18 may be actuated, for example, by depressing a main switch 90 located on the top of the housing 38 (FIGS. 7 and 7a). Next, the desired radiation type may be selected by rotating the dial 70 until visible indicia 92, such as the alignable markings shown in FIGS. 7 and 7a, indicate proper dial positioning for the given source 36 or 72. Once selected, the source 36 or 72 becomes energized, thereby producing the desired radiation. Indicator lights 94,96 are provided on top of the housing to further indicate the activation of the selected source 36 or 72. As shown in FIGS. 5 and 6, the preferred indicator lights 94,96 are produced by energizing an LED in series connection to the particular source 36 or 72. The preferred indicator lights 94,96 present different colors for distinguish the light sources 36,72; for example, a blue LED may be utilized in conjunction with a UV source 72, and a yellow LED with a visible light source 36.

3. Additional Configurations and Features.

As discussed, in one configuration the apparatus 10 may include an illuminator 18 operable to produce light, and a rigidly flexible light pipe 16 to deliver the generated light to a particular place on or in a patient. The illuminator 18 may use a light emitting diode (LED) 36 controlled by electronics that respond to input by a healthcare practitioner to generate the light having a desired wavelength or range of wavelengths and a desired intensity. The light may be adjustable to include ultraviolet light with a wavelength as short as approximately 100 nm, infrared light with a wavelength as long as approximately 15,000 nm, or any combination of wavelengths therebetween. For example, the illuminator 18 may be operable to pass a selectable range of wavelengths (in the manner of a band-pass filter), or to reject a selectable subrange of wavelengths (in the manner of a band-rejection filter). Use of the electronically controlled LED provides a number of advantages, including eliminating the need for multiple lights, each operable to produce only particular wavelengths, and minimizing exposure of the patient to damaging heat, relative to other types of light sources. The light pipe 16 may be at least approximately two feet in length, able to be repeatedly and inelastically bent or otherwise repositioned with regard to the patient, and have a fiber optic core to facilitate delivery of the light. The apparatus 10 may be adapted for use by any sort of healthcare practitioner, including dentists, surgeons, oncologists, and others, to meet their specific needs and desires in performing their particular procedures.

Referring to FIGS. 8-14, additional configurations of the light apparatus are shown and herein described. These additional configurations may be substantially similar or even identical to or simply incorporate any one or more features of, any one or more of the other herein-described configurations, except as noted.

Figure 8:
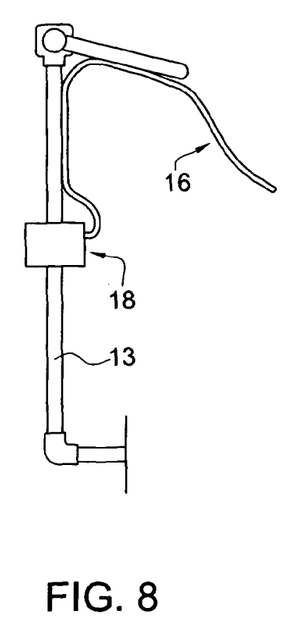
FIG. 8 is a side elevation view of portions of the apparatus mounted to a fixed pole.
Figure 9:
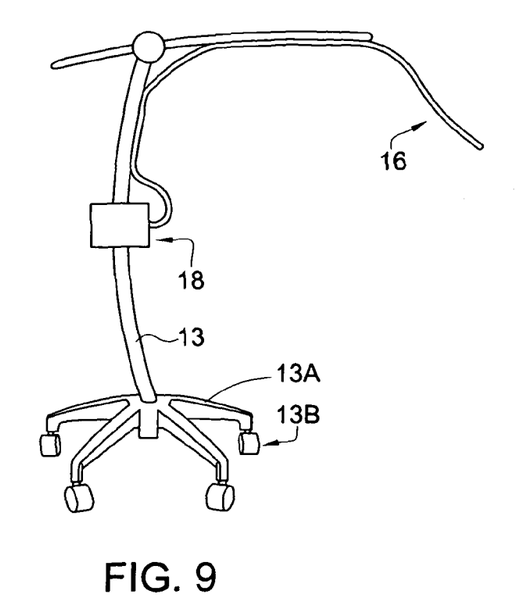
FIG. 9 is a side elevation view of portions of the apparatus mounted to a wheeled base.
Figure 10:
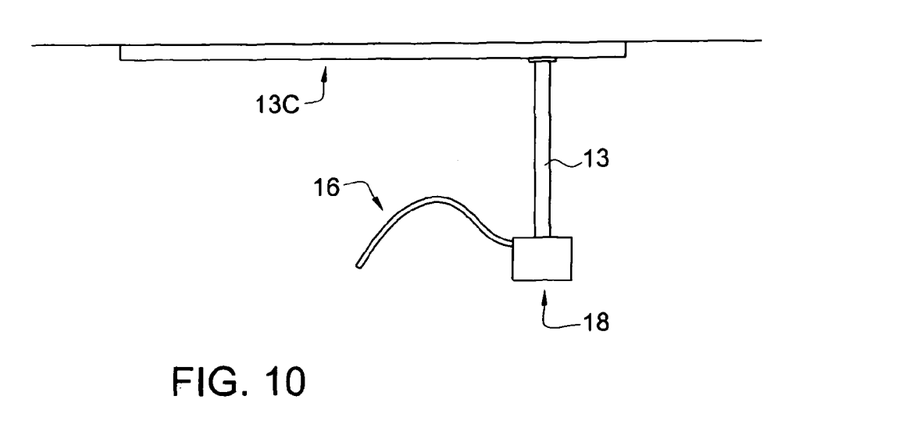
FIG. 10 is a side elevation view of portions of the apparatus slidably mounted to a track.

Additional configurations are contemplated that are substantially independent of both the headrest and the chair. In one such configuration, the illuminator 18 and the light pipe 16 may be unmounted and simply sit on a countertop or other convenient flat surface (see FIG. 14). FIG. 8 shows the illuminator 18 and the light pipe 16 mounted to a pole 13. The pole 13 may, in turn, be mounted to a wall, a ceiling, a floor, a counter, or some other structure or surface. FIG. 9 shows the illuminator 18 and the light pipe 16 mounted to the pole 13, the pole 13 mounted to a base 13a, and the base provided with a plurality of wheels, casters, or other rollable members 13b to facilitate rolling movement. FIG. 10 shows the illuminator 18 and the light pipe 16 mounted to the pole 13, and the pole 13 movably, e.g., slidably or rollably, mounted to a track 13c. The track 13c may, in turn, be mounted to a wall, a ceiling, a floor, a counter or some other structure or surface.

Figure 11:
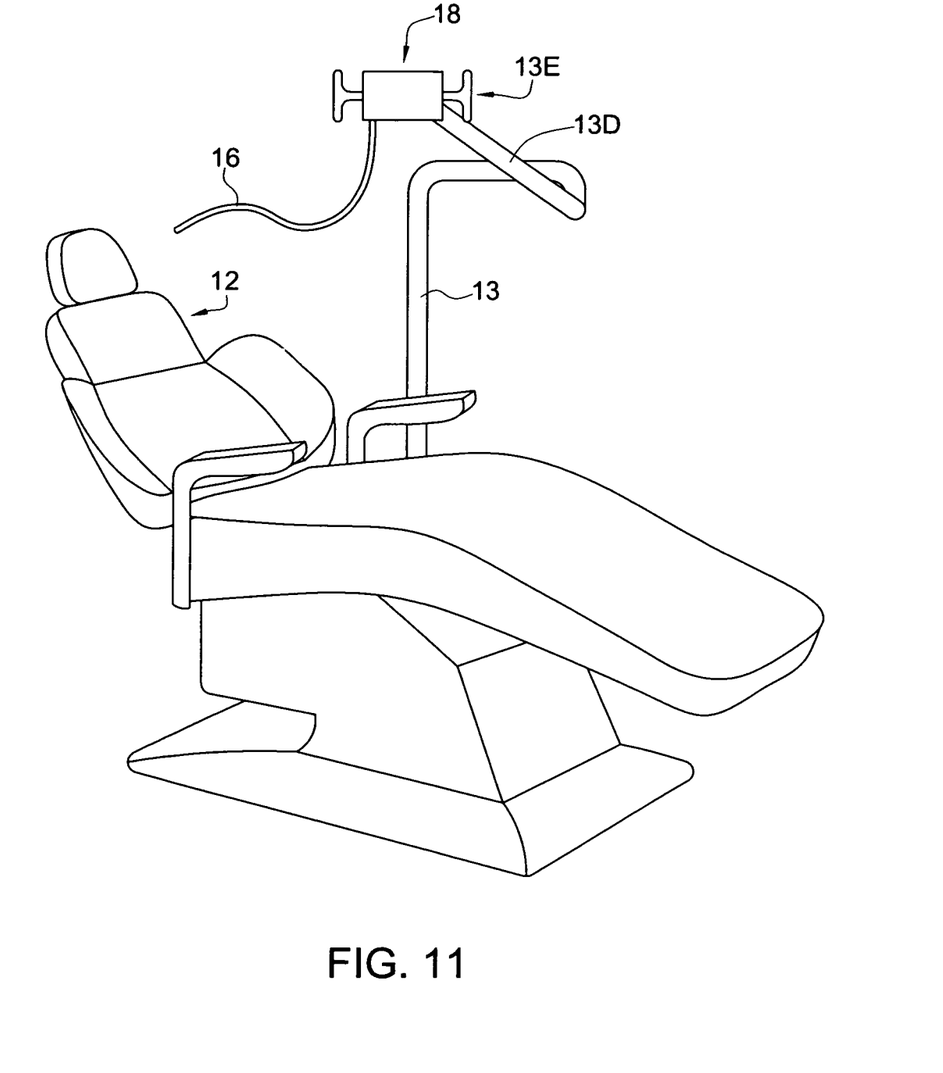
FIG. 11 is a perspective view of portions of the apparatus mounted to a positionable arm.

FIG. 11 shows the illuminator 18 and the light pipe 16 mounted to an arm 13d, which is, in turn, positionably mounted to the pole 13, which is mounted to the chair 12. The illuminator 18 may be provided with handles 13e that can be grasped in order to more conveniently reposition the arm 13d and illuminator 18 mounted thereto.

Figure 12:
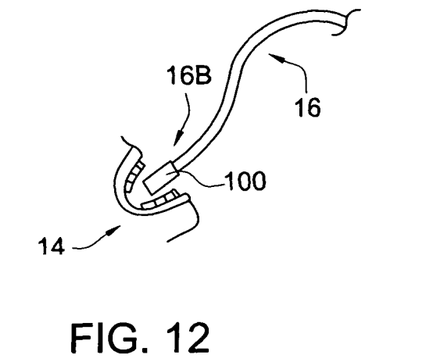
FIG. 12 is a side elevation view of a camera component mounted to an end of a portion of the apparatus.

Referring to FIG. 12, any of the herein-described configurations of the light apparatus may further include a wired or wireless digital camera 100 that may be permanently attached or removably attachable at or adjacent to the light emitting outlet 16b of the light pipe 16. This feature advantageously allows the healthcare practitioner to easily and conveniently position the camera 100 adjacent to the body part, e.g., the tooth or teeth, being imaged.

Figure 13:
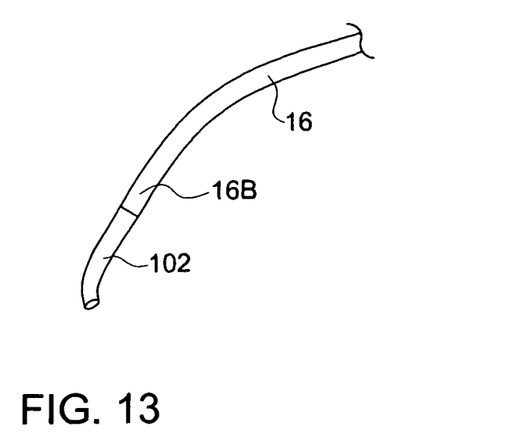
FIG. 13 is a side elevation view of an illuminator tip component mounted to an end of a portion of the apparatus.

Referring to FIG. 13, any of the herein-described configurations of the apparatus may further include an illuminator tip 102 that may be permanently attached or removably attachable at or adjacent to the light emitting outlet 16b of the light pipe 16. This feature advantageously allows the healthcare practitioner to easily and conveniently direct high-intensity light through bodily tissue and thereby inspect the interior of the tissue without exposing the patient to X-rays. For example, a dental practitioner may use the illuminator tip 102 to direct high intensity light through a tooth and thereby see cracks, fractures, and decay. The illuminator tip 102 may be curved to facilitate positioning the tip behind the tooth or other bodily tissue so that the light shines through it.

Figure 14:
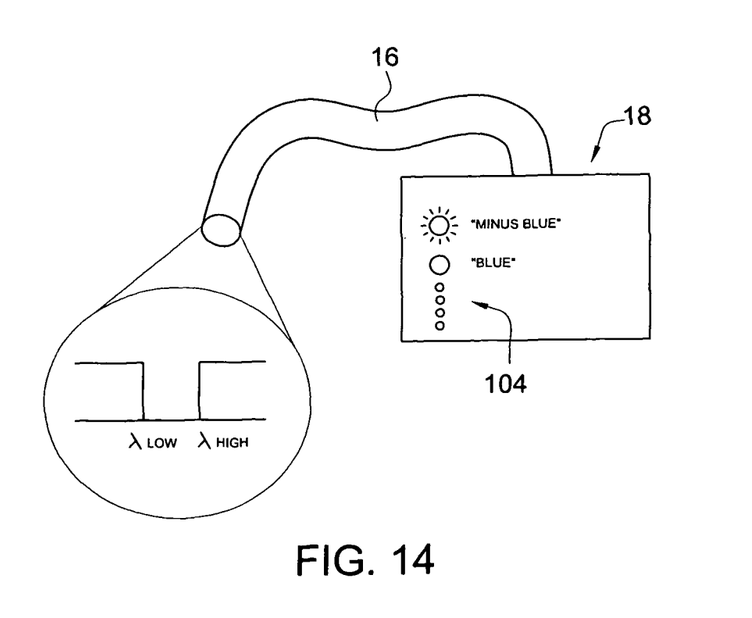
FIG. 14 is a depiction of a band-rejection function of the apparatus.

Referring to FIG. 14, any of the herein-described configurations of the light apparatus may include the ability to eliminate particular wavelengths or ranges of wavelengths, i.e., $\lambda_{LOW}$ to $\lambda_{HIGH}$, from the emitted light. As mentioned, certain materials, e.g., dental filling materials, are applied in a monomeric or other relatively fluid state and then photopolymerized, i.e., "cured", under blue light having a wavelength approximately between 250 to 500 nm. Often, these materials are applied under normal office illumination which includes the activating wavelength(s), and, as such, the material is polymerizing as the practitioner works. This is particularly problematic when a relatively large amount of the material must be applied, such as when multiple teeth must be filled, during a single procedure. The illuminator 18 advantageously overcomes this problem by including a setting that provides visible light minus the particular activating wavelength(s), i.e., the illuminator 18 can act in the manner of a band-stop or band-rejection filter. The illuminator 18 may also provide a setting that provides only the particular activating wavelength(s). Thus, once the material has been applied under "minus blue" light, the practitioner can selectively cause the illuminator 18 to produce the "blue" light which polymerizes or otherwise activates the material. When implemented using an LED, this feature is particularly advantageous in that it both eliminates the need for multiple lights, each operable to produce only particular wavelengths, and provides higher power pulsed light that polymerizes the material in less time and with less exposure to damaging heat than other types of light sources.

Relatedly, the apparatus may further include a timer feature 104 operable to automatically revert to the minus "blue light" or other broad spectrum light after a set period of time. For example, the practitioner may be able to select a multiple of 10, 15, or 30 second periods, depending on the desired length of curing time, during which the blue light is emitted, and at the end of which the illuminator 18 automatically switches to emitting the broader spectrum light. In one contemplated version of this feature, the practitioner depresses the "blue" button a number of times equal to the number of desired periods, and a series of lights or a digital timer on the face of the illuminator 18 indicates the number of periods remaining before the illuminator 18 reverts to the broader spectrum light.

Any of the herein-described configurations of the light apparatus may further include a "shade matching" feature. More specifically, the coloration of certain materials, e.g., porcelain dental veneer, tends to change under different light. The illuminator 18 may be operable to produce different types of common light so that the materials can be viewed under those lights prior to their application. For example, a dental practitioner may be able to selectively cause the illuminator 18 to produce any of several common types of light, such as incandescent light, natural sunlight, and fluorescent light, having particular wavelength(s) to facilitate the selection of a particular shade of veneer that appeals to the patient.

Any of the herein-described configurations of the light apparatus may further include a bleaching feature wherein the illuminator 18 is operable to produce the particular wavelength(s) of light that activate a bleaching compound, such as compound used to bleach teeth.

Any of the herein described configurations of the light apparatus may further include a cancer screening feature wherein the illuminator 18 is operable to produce the particular wavelength(s) of light that cause cancerous cells, such as oral cancer cells, painted with a particular solution to fluoresce or otherwise activate.

The preferred forms of the invention described above are to be used as illustration only, and should not be utilized in a limiting sense in interpreting the scope of the general inventive concept. Obvious modifications to the exemplary embodiments and methods of operation, as set forth herein, could be readily made by those skilled in the art without departing from the spirit of the present invention. The inventor hereby states his intent to rely on the Doctrine of Equivalents to determine and assess the reasonably fair scope of the present invention as pertains to any system or method not materially departing from but outside the literal scope of the invention as set forth in the following claims.

The invention claimed is:

1. A headrest adapted for use and interconnection with a healthcare practitioner's chair, and for supporting a head of and illuminating a patient positioned within the chair, said headrest comprising:
    a light source configured to produce a quantity of light having a minimum luminosity value when energized;
    a light pipe defining an inlet communicatively coupled to the light source, a longitudinal pipe length, and an outlet positioned at a first location and configured to transmit the light towards the patient;
    a housing supporting and configured to retain the light source, securely coupled to the light pipe, and presenting a soft exterior surface defining a shape, orientation, and surface area operable to support the head of the patient when the patient is positioned within the chair; and
    a power supply communicatively coupled to and operable to selectively energize the light source.

2. The headrest as claimed in claim 1, wherein at least a portion of the light pipe is rigidly flexible, so as to be adjustably bendable to one of a plurality of functional conditions wherein the outlet is manually repositioned to a second location spaced apart from the first.

3. The headrest as claimed in claim 1, further including an interconnection mechanism fixedly secured to the housing, and cooperatively configured with the chair, so as to enable the manual connection and disconnection of the headrest and chair.

4. A headrest adapted for use and interconnection with a healthcare practitioner's chair, and for supporting the head of and illuminating a patient positioned within the chair, said headrest comprising:
    a light source including at least one light emitting diode and configured to produce light having a desired wavelength;
    a rigidly flexible light pipe attached to the light source to deliver the light to a particular place, wherein the light pipe is able to be repeatedly repositioned by bending, and has a fiber optic core to deliver the light;
    a housing supporting and configured to retain the light source, securely coupled to the pipe, and presenting a soft exterior surface defining a shape, orientation, and surface area operable to support the head of the patient, when the patient is positioned within the chair; and
    a power supply communicatively coupled to and operable to selectively energize the light source.

5. The headrest as set forth in claim 4, wherein the light source is operable to produce the light having a wavelength between ultraviolet light and infrared light.

6. The headrest as set forth in claim 4, wherein the light source is operable to produce the light having a selectable range of different wavelengths associated with incandescent light, natural sunlight, and fluorescent light.

7. The headrest as set forth in claim 6, wherein the light source is selectively operable to eliminate a subrange of wavelengths from the range of wavelengths.

8. The headrest as set forth in claim 7, wherein the range of wavelengths includes visible light, the subrange of wavelengths includes a wavelength operable to polymerize a compound.

9. The headrest as set forth in claim 7, wherein the light source is operable to produce the light having only the subrange of wavelengths.

10. The headrest as set forth in claim 9, wherein the light source includes a timer operable to produce the light having only the subrange of wavelengths for a selected period of time, and at the end of the selected period of time, automatically revert to producing the light having the range of wavelengths.

11. The headrest as set forth in claim 9, wherein the subrange of wavelengths is operable to activate a bleaching compound.

12. The headrest as set forth in claim 4, further including a digital camera attachable to a light emitting end of the light pipe and operable to capture digital images.

13. The headrest as set forth in claim 4, further including an illuminator tip attachable to a light emitting end of the light pipe and operable to increase the intensity of the light.

14. The headrest as set forth in claim 13, wherein the illuminator tip is curved to facilitate delivering the light to a particular place.

15. A headrest adapted for use with a healthcare practitioner's chair, and for illuminating a patient positioned within the chair, said headrest comprising:
    a light source including at least one light emitting diode configured to produce light having a desired wavelength between ultraviolet light and infrared light;
    a rigidly flexible light pipe attached to the light source to deliver the light to a particular place, wherein the light pipe is able to be repeatedly repositioned by bending, and has a fiber optic core to deliver the light;

a housing supporting and configured to retain the light source, securely coupled to the pipe, and presenting a soft exterior surface operable to support the head of the patient, when the patient is positioned within the chair; and a power supply communicatively coupled to and operable to selectively energize the light source.

16. The headrest as set forth in claim 15, wherein the light source includes electronics to:

produce the light having a selectable range of different wavelengths associated with incandescent light, natural sunlight, and fluorescent light;

eliminate a subrange of wavelengths from the range of wavelengths, wherein the subrange of wavelengths includes a wavelength operable to polymerize a compound;

produce the light having only the subrange of wavelengths; and produce the light having only the subrange of wavelengths for a selected period of time, and, at the end of the selected period of time, automatically cease providing the light having the range of wavelengths.

17. The headrest as set forth in claim 16, wherein the subrange of wavelengths is operable to activate a bleaching compound.

18. The headrest as set forth in claim 15, further including a digital camera attachable to a light emitting end of the light pipe and operable to capture digital images.

\* \* \* \* \*